US007087391B2

(12) United States Patent
Yamagishi et al.

(10) Patent No.: US 7,087,391 B2
(45) Date of Patent: Aug. 8, 2006

(54) ANTIBODY TO HEPATOCYTE GROWTH FACTOR ACTIVATOR INHIBITOR-1 AND USE THEREOF

(75) Inventors: Toshiya Yamagishi, Yokohama (JP); Daiji Naka, Yokohama (JP); Kazuhiro Nagaike, Inashiki-gun (JP)

(73) Assignee: Mitsubishi Chemical Corporation, Tokyo (JP)

( * ) Notice: Subject to any disclaimer, the term of this patent is extended or adjusted under 35 U.S.C. 154(b) by 362 days.

(21) Appl. No.: 10/153,661

(22) Filed: May 24, 2002

(65) Prior Publication Data

US 2003/0064420 A1    Apr. 3, 2003

(30) Foreign Application Priority Data

May 25, 2001 (JP) .............................. 2001-157082
Jan. 16, 2002 (JP) .............................. 2002-007443

(51) Int. Cl.
*G01N 33/53* (2006.01)
*C12N 5/00* (2006.01)
*C07K 16/00* (2006.01)
*C12P 21/08* (2006.01)

(52) U.S. Cl. ....................... 435/7.1; 435/346; 435/810; 530/387.9; 530/388.1

(58) Field of Classification Search ............. 530/387.9, 530/388.1; 435/346, 810, 7.1
See application file for complete search history.

(56) References Cited

U.S. PATENT DOCUMENTS 4,281,061 A * 7/1981 Zuk et al. ..................... 435/7.9
6,225,081 B1 * 5/2001 Shimomura et al. ......... 435/69.1

FOREIGN PATENT DOCUMENTS

| EP | 0 759 467 | | 2/1997 |
| JP | 11-035480 | | 2/1999 |
| JP | 11-295309 | | 10/1999 |
| WO | WO 01/68707 | * | 9/2001 |

OTHER PUBLICATIONS

Goldsby et al., Immunology, Fifth edition, 2000, pp. 137-139.*
Hiroaki Kataoka et al., "Hepatocyte Growth Factor Activator Inhibitor Type 1 is a Specific Cell Surface Binding Protein of Hepatocyte Growth Factor Activator (HGFA) and Regulates HGFA Activity in the Pericellular Microenvironment", The Journal of Biological Chemistry, vol. 275, No. 51, pp. 40453-40462, Dec. 22, 2000.
Hiroaki Kataoka et al., "Distribution of Hepatocyte Growth Factor Activator Inhibitor Type 1 (HAI-1) in Human Tissues: Cellular Surface Localization of HAI-1 in Simple Columnar Epithelium and its Modulated Expression in Injured and Regenerative Tissues", The Journal of Histochemistry & Cytochemistry, vol. 47, No. 5, pp. 673-682, May 1999.
Takeshi Shimomura et al., "Multiple Sites of Proteolytic Cleavage to Release Soluble Forms of Hepatocyte Growth Factor Activator Inhibitor Type 1 from a Transmembrane Form", Journal of Biochemistry, vol. 126, No. 5, pp. 821-828, Nov. 1999.
Chen-Yong Lin et al., "Purification and Characterization of a Complex Containing Matriptase and a Kunitz-Type Serine Protease Inhibitor from Human Milk", The Journal of Biological Chemistry, vol. 274, No. 26, Jun. 25, 1999, pp. 18237-18242.
Hiroshi Itoh et al., "Upregulation of HGF Activator Inhibitor Type 1 But Not Type 2 Along with Regeneration of Intestinal Mucosa", Am. J. Physiol. Gastrointest. Liver Physiol. vol. 278, pp. G635-G643, 2000.
Hiroshi Itoh et al., "Genomic Structure and Chromosomal Localization of the Human Hepatocyte Growth Factor Activator Inhibitor Type 1 and 2 Genes", Eur. J. Biochem., vol. 267, pp. 3351-3359, FEBS 2000.
Hiroaki Kataoka et al., "Activation of Hepatocyte Growth Factor/Scatter Factor in Colorectal Carcinoma", Cancer Research, vol. 60, pp. 6148-6159, Nov. 1, 2000.
Michael Oberst et al., "Matriptase and HAI-1 are Expressed by Normal and Malignant Epithelial Cells *in vitro* and *in vivo*", American Journal of Pathology, vol. 158, No. 4, pp. 1301-1311, Apr. 2001.

* cited by examiner

*Primary Examiner*—Christina Chan
*Assistant Examiner*—Michail Belyavskyi
(74) *Attorney, Agent, or Firm*—Wenderoth, Lind & Ponack, L.L.P.

(57) ABSTRACT

A hybridoma is selected that produces a monoclonal antibody exhibiting high reactivity to soluble hepatocyte growth factor activator inhibitor-1 (soluble HAI-1), the target monoclonal antibody is prepared from culture supernatant of the obtained hybridoma, and by using the antibody soluble HAI-1 is measured.

9 Claims, 2 Drawing Sheets

A

B

ANTIBODY TO HEPATOCYTE GROWTH FACTOR ACTIVATOR INHIBITOR-1 AND USE THEREOF

BACKGROUND OF THE INVENTION

1. Field of the Invention

The present invention relates to an antibody or a monoclonal antibody for quantitative determination of hepatocyte growth factor activator inhibitor-1 (hereinafter, sometimes abbreviated as "HAI-1"), to a method of using the same and to a kit for measuring the same. Also, the present invention relates to a method of detecting and measuring the state of a patient suffering from a disease, In particular inflammation of an organ, nephritis, cancers, liver diseases, blood diseases, myocardial infarction, angina pectoris, cerebral infarction, or thrombosis.

2. Description of the Related Art

The hepatocyte growth factor activator inhibitor-1 (HAI-1) is known as a control agent for a hepatocyte growth factor inhibitor and as a kind of Kuniz type serine protease inhibitor (Shimomura et al., J. Biol. Chem., 272: 6370–6376 (1997)). HAI-1 is considered to be a protein that has a portion that penetrates through a cytoplasmic membrane (hereinafter, referred to as "cytoplasmic membrane-penetrating portion") and is reported to have a molecular weight of about 66,000 (electrophoresis) (Shimomura et al., J. Biol. Chem., 126: 821–828 (1999)). Also, HAI-1 is known to exist in the supernatant of a culture of HAI-1-producing culture cells, such as MKN45, in a state where it has no cytoplasmic membrane-penetrating portion. It has been reported through the measurement by using an SDS-PAGE method under the reduction condition that these soluble HAI-1 molecules include a molecule having a molecular weight of about 58,000, a molecule having a molecular weight of about 48,000, a molecule having a molecular weight of about 40,000, and a molecule having a molecular weight of about 39,000, which are called "soluble forms of HAI" (Shimomura et al., J. Biol. Chem., 126: 821–828 (1999)); herein these are referred to as "soluble HAI-1."

It has been known that HAI-1 has the effect of a protease inhibitor such as the effect of inhibiting a hepatocyte growth factor-activating factor [which is a factor that acts on a hepatocyte growth factor (hereinafter, abbreviated as "HGF" (Naka et al., J. Biochem., 267: 20114–20119 (1992)) and subjecting it to specific restricted decomposition to activate it (Shimomura et al., Cytotechnology, 8:219–229 (1992))]. The known antibody to HAI-1 includes murine monoclonal antibodies C76-18 and 1N7 (Shimomura et al., JP 11-295309 A: C76-18, Kataoka et al., J. Histochem. Cytochem., 47: 673–682 (1999): 1N7). Tissue staining using this antibody has revealed that HAI-1 is expressed in pancreas, liver, small intestine and uterus of normal persons. Tissue staining using the above-mentioned antibody has been performed for patients suffering from liver cancer and expression of HAI-1 has been examined (Kataoka et al., Cancer Research, 60, 6148–6159, 2000). However, the role and function of HAI-1 in human pathology have not been clarified yet. Further, the relationship between the concentration of soluble HAI-1 in the biological components such as blood and the pathology has not been known.

To analyze the relationship between the concentration of soluble HAI-1 in the biological components, such as blood level, and the pathology, it is necessary to quantitatively determine soluble HAI-1 that exists in the biological components such as human tissue, body fluid, urine or blood. Then, to quantitatively determine soluble HAI-1, it is indispensable to obtain a high-affinity antibody that recognizes soluble HAI-1, particularly desirably a high-affinity monoclonal antibody.

The known antibody to HAI-1 includes murine monoclonal antibodies C76-18 and 1N7 (Shimomura et al., JP 11-295309 A: C76-18, Kataoka et al., J. Histochem. Cytochem., 47: 673–682 (1999): 1N7). However, there has been no anti-soluble HAI-1 antibody having suitable properties for quantitatively determining soluble HAI-1 or no method or kit therefor for detecting or quantitatively determining soluble HAI-1 existing in the biological components such as human blood.

SUMMARY OF THE INVENTION

An object of the present invention is to provide a method of detecting soluble HAI-1 by using a high-affinity antibody that recognizes the soluble HAI-1, a method of quantitatively determining the same and a method of detecting a disease associated with soluble HAI-1, a method of quantitatively determining the same and a kit therefor.

The above-mentioned murine monoclonal antibodies to HAI-1, i.e., C76-18 and 1N7 (Shimomura et al., JP 11-295309 A: C76-18, Kataoka et al., J. Histochem. Cytochem., 47: 673–682 (1999): 1N7) are not suitable for quantitatively determining soluble HAI-1 in the biological components. In fact, attempts to construct a measurement system for measuring soluble HAI-1 by using obtained such existing antibodies have failed to realize construction of a system that allows determination of the concentration of soluble HAI-1 in blood. The reason for this would be as follows. That is, it is because although the existing antibodies could recognize HAI-1 on the surface of cells but could not recognize soluble HAI-1 such as one that exists in biological components such as blood or urine. Alternatively, it is because the existing antibodies might have low affinity for HAI-1 and could not sufficiently bind to soluble HAI-1 in the biological components. In fact the dissociation constants of the existing antibodies to HAI-1 measured are C76-18: $Kd=1.48\times10^{-9}$ M, and 1N7: $Kd=1.68\times10^{-8}$ M, which correspond to insufficient affinity for the measurement of concentrations of soluble HAI-1 in the biological components in human.

On the other hand, as a result of extensive studies, the inventors of the present invention were successful in obtaining a high-affinity murine monoclonal antibody to the soluble HAI-1. The high-affinity murine monoclonal antibody to the soluble HAI-1: HAI-1A-1-1-3-4, which the inventors have obtained has a dissociation constant of antigen-antibody reaction of $Kd=2.67\times10^{-10}$ M, which is considerably higher in affinity than that of conventional antibodies, and also has sufficient affinity for determining the concentration of soluble HAI-1 in the biological components in human. Thus, the inventors successfully constructed a quantitative determination system by using such an antibody. Further, it revealed that the antibody of the present invention has enough affinity to analyze the relationship between the concentration of soluble HAI-1 and various human diseases in human pathology.

Accordingly, to analyze the relationship between the concentration of soluble HAI-1 in blood in human pathology and various human diseases, the inventors contemplated to construct a highly sensitive quantitative determination system for determining HAI-1 in human blood by using a high-affinity antibody HAI-1A-1-1-3-4. That is, an enzyme-linked immunosorbent assay (hereinafter, abbreviated as "ELISA assay system" using a double antibody sandwich method utilizing a murine monoclonal antibody HAI-1A-1-1-3-4 against soluble HAI-1 and a rabbit polyclonal antibody was constructed and the concentration of soluble HAI-1 was measured for bloods (blood plasmas or sera) of healthy persons and patients suffering from various diseases such as a disease of an organ.

As a result, by using the soluble HAI-1-specific highly sensitive measurement method and a kit therefor according to the present invention, the inventors have clarified the blood level range of soluble HAI-1 in a healthy person for the first time and found a considerable increase in the amount of soluble HAI-1 existing in the blood of patients suffering from organopathy such as glomerulonephritis or the like, cancers or thrombosis.

The present invention has been accomplished based on these findings and provides the followings.

(1) An antibody that recognizes and quantitatively binds to soluble hepatocyte growth factor activator inhibitor-1 (soluble HAI-1).

(2) The antibody according to (1), wherein the soluble HAI-1 has a molecular weight of about 39,000 to 58,000 daltons as measured by SDS-PAGE under reduced conditions.

(3) The antibody according to (1) or (2), wherein the antibody has a dissociation constant with respect to the soluble HAI-1 of $2 \times 10^{-9}$ M or less.

(4) The antibody according to any one of (1) to (3), wherein the antibody is a monoclonal antibody.

(5) A monoclonal antibody according to (4), wherein the antibody is produced by the hybridoma of which accession number is FERM BP-8022.

(6) A hybridoma cell line that produces a monoclonal antibody according to (4).

(7) The hybridoma cell line according to (6), wherein the cell line is the hybridoma of which accession number is FERM BP-8022.

(8) A method of quantitatively determining soluble HAI-1, comprising immunologically measuring the soluble HAI-1 by using one or a plurality of antibodies according to any one of (1) to (5).

(9) The method according to (8), wherein a sample in which soluble HAI-1 is to be measured is a biological component collected from a subject or animal suspected of a disease.

(10) The method according to (9), wherein the disease is selected from the group consisting of organ inflammation, nephritis, cancers, liver diseases, blood diseases, myocardial infarction, angina pectoris, cerebral infarction and thrombosis.

(11) The method according to (9), wherein the disease is hepatocellular carcinoma or pancreas cancer.

(12) The method of detecting a disease comprising detecting or measuring soluble HAI-1 in a biological component collected from a subject suspected of the disease.

(13) The method according to (12), wherein the disease selected from the group consisting of organ inflammation, nephritis, cancers, liver diseases, blood diseases, myocardial infarction, angina pectoris, cerebral infarction and thrombosis.

(14) The method according to (12), wherein the disease is selected from the group consisting of hepatocellular carcinoma and pancreas cancer.

(15) The method according to (9) or (12), wherein the biological component is blood or its fractionation product or a treated product.

(16) The method according to claim (9) or (12), wherein the biological component is plasma or blood serum.

(17) The method according to claim (9) or (12), wherein the biological component is urine.

(18) A kit for detecting or quantitatively determining soluble HAI-1, comprising one or a plurality of antibodies according to (1).

(19) The kit according to (18), wherein the kit is used for the diagnosis of at least one disease selected from the group consisting of organ inflammation, nephritis, cancers, liver diseases, blood diseases, myocardial infarction, angina pectoris, cerebral infarction and thrombosis.

(20) The kit according to (18), wherein soluble HAI-1 in a biological component collected from a patient suspected of a disease is measured with the kit.

(21) The kit according to (18), wherein the detection or measurement of the soluble HAI-1 is performed by immunological staining.

In this specification, the monoclonal antibody that recognizes soluble HAI-1 is sometimes referred to as "soluble HAI-1-specific high-affinity monoclonal antibody" and the polyclonal antibody that recognizes soluble HAI-1 is sometimes referred to as "soluble HAI-1-specific polyclonal antibody." Further, these antibodies may be collectively referred to as "soluble HAI-1-specific high-affinity" antibody. Furthermore, the phraseology "recognizes soluble HAI-1" means that an antibody "binds to soluble HAI-1 by an antigen-antibody reaction." In this case, the soluble HAI-1-specific high-affinity antibody of the present invention may bind to either full-length HAI-1 or a part thereof.

The phraseology "quantitatively binds" as used herein means that the antibody binds to such an extent that it is possible to detect the binding between the soluble HAI-1-specific high-affinity antibody of the present invention and soluble HAI-1 in correlation with the concentration of soluble HAI-1. Specifically, it means that the antibody binds to such an extent that it is possible to quantitatively determine soluble HAI-1 by an immunological method such as enzyme immunoassay, radioimmunoassay, fluorescence immunoassay, chemiluminescence immunoassay, immunoblotting, immunochromatography, or latex agglutination. For example, antibodies that enable quantitative determination of soluble HAI-1 in an amount of 10 ng/ml or more, preferably 1 ng/ml or more, and more preferably 0.5 ng/ml or more may be used as the soluble HAI-1-specific high-affinity antibody of the present invention.

According to the present invention monoclonal antibodies and polyclonal antibodies that specifically bind to soluble HAI-1 can be provided. The antibodies of the present invention can be used for specific and highly sensitive measurement and detection of soluble HAI-1.

The method of measuring soluble HAI-1 according to the present invention can be utilized for the diagnosis of various diseases reflected by the blood level of soluble HAI-1.

DETAILED DESCRIPTION OF THE INVENTION

Figure 1:
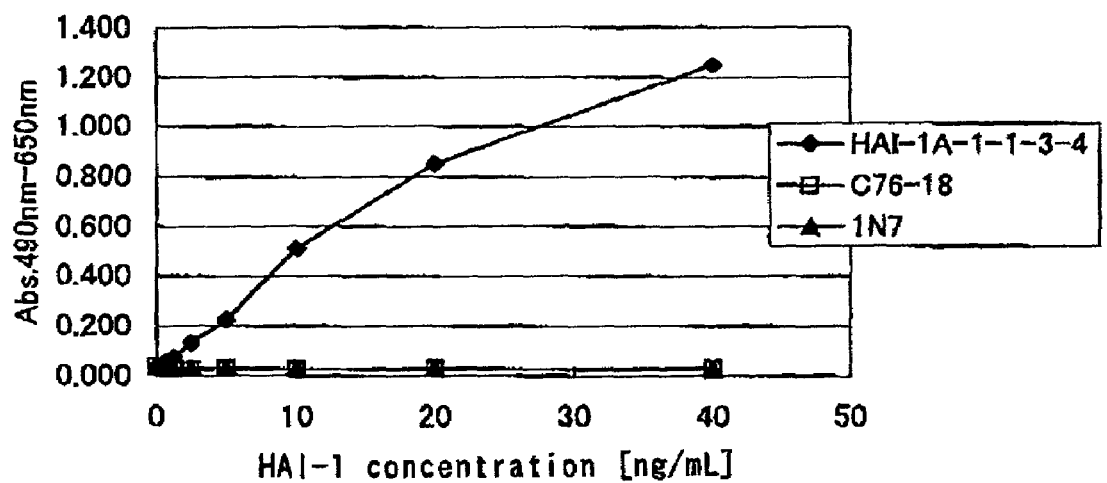
FIG. 1A is a diagram illustrating the reactivity between standard HAI-1 and each monoclonal antibody in an HAI-1 measuring system in a concentration of HAI-1 in a range of from 0 to 40 ng/ml.
FIG. 1B is a diagram illustrating the reactivity between standard HAI-1 and each monoclonal antibody in an HAI-1 measuring system in a concentration of HAI-1 in a range of from 0 to 2.5 ng/ml out of the range shown in FIG. 1A in an enlarged view in which a closed rhombus ( )indicates HAI-1A-1-1-3-4; an open square ( ) indicates C76-18; and a triangle indicates IN7.
Figure 1:
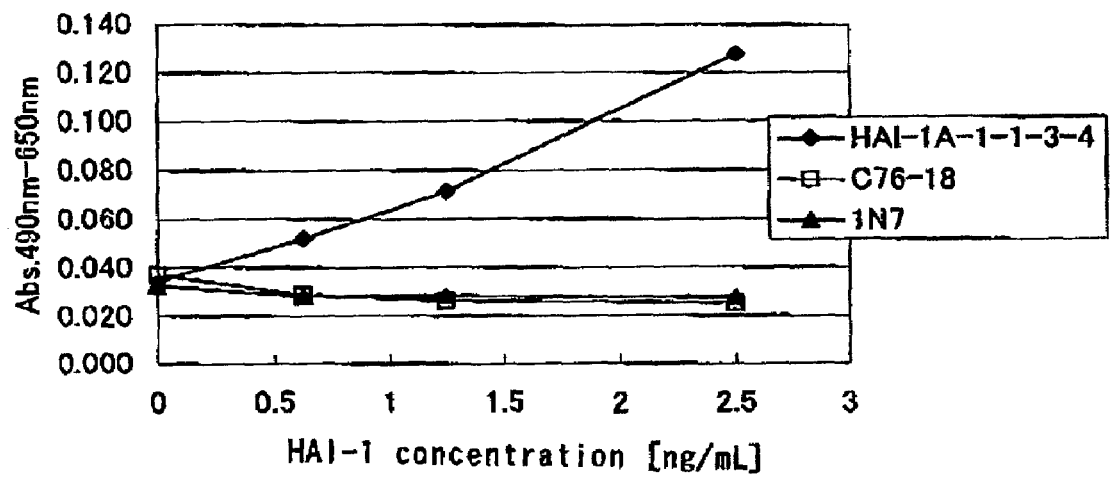

Hereinafter, the present invention will be described in detail.

<1> Immunogen and Screening Antibody for Preparing Soluble HAI-1-Specific High-Affinity Antibody HAI-1 for use as an immunogen may be a full-length HAI-1 or a soluble HAI-1, i.e., an extracellular domain of HAI-1 or its partial peptide. To efficiently obtain a soluble HAI-1-specific high-affinity antibody, it is preferred to use soluble HAI-1 or its partial peptide. At least one of the immunogen and HAI-1 used for screening monoclonal antibody is preferably soluble HAI-1 or a partial peptide thereof.

As the soluble HAI-1, for example, purified supernatant of a culture of HAI-1-producing cell line, for example, MKN45, obtained according to the method of Shimomura et al. (J. Biol. Chem., 272: 7370–6370 (1997)) can be used. Also, HAI-1 which is recombinant protein produced by microorganism such as *Escherichia coli*, insect cells, yeast, animal cells and animals utilizing HAI-1 cDNA described in JP 9-95497 A (U.S. Pat. No. 6,225,081) can be utilized. Furthermore, peptides having a partial sequence of HAI-1 prepared by chemical synthesis can be utilized.

In particular, to obtain HAI-1-specific high-affinity antibody, it is preferred to prepare high-purity HAI-1. For this purpose, the HAI-1 as used herein, recombinant protein prepared by using HAI-1 cDNA is desirable. For example, recombinant HAI-1 can be obtained by inserting HAI-1 cDNA encoding HAI-1 as described in JP 9-95497 A (U.S. Pat. No. 6,225,081) in its entire length or a part thereof into a suitable expression vector, introducing the expression vector into a microorganism such as *Escherichia coli*, an insect cell, yeast, an animal cell or an animal, and subjecting the supernatant of a culture of such a transgenic cell or intracellular fraction, tissue or body fluid that expresses HAI-1 to purification operation. In a case where animal cells suitable as a host for expressing the above-mentioned cDNA, for example, CHO cells are used, soluble HAI-1 is liberated in a culture supernatant, on the other hand, in a case where microbial cells are used as a host, a region that encodes an extracellular domain out of the HAI-1 cDNA may be expressed. Furthermore, a suitable secretion signal may be used if necessary.

It is also possible to prepare the target HAI-1 by using in vitro transcription/translation system using Rapid Translation System RTS500 (Roche Diagnostics Co.) without using any cell system.

As a specific example thereof, it is possible to obtain soluble HAI-1, which is a recombinant protein, by introducing an expression vector having inserted the HAI-1 cDNA described in JP 9-95497 A (U.S. Pat. No. 6,225,081) downstream of the promoter of an animal cell expression vector, into an animal cell, selecting a cell that expresses HAI-1 cDNA, and purifying soluble HAI-1 from a supernatant of the culture. The purification of soluble HAI-1 can be performed by ordinary purification methods for proteins, such as gel filtration by using HPLC or affinity chromatography.

Soluble HAI-1 having high purity is not only important as an immunogen but also very important as a material for separating a soluble HAI-1-specific polyclonal antibody by affinity purification and for screening a soluble HAI-1-specific high-affinity monoclonal antibody. Also, it is important as a standard preparation of soluble HAI-1 at the time of quantitative determination.

<2> Preparation of Soluble HAI-1-Specific High-Affinity Monoclonal Antibody

To obtain a soluble HAI-1-specific high-affinity monoclonal antibody, an immunological method usually used may be practiced by using the above-mentioned HAI-1, preferably soluble HAI-1, as an antigen for immunization.

The animals to be used for immunization are not particularly limited and any one of rabbit, goat, sheep, mouse, rat, guinea pig, and chicken may be used. Inoculation of the antigen for immunization to an animal is performed subcutaneously, intramuscularly, or intraperitoneally after well mixing the antigen for immunization with Complete Freund's adjuvant or Incomplete Freund's adjuvant. The inoculation is practiced every 2 weeks to 5 weeks and continued until the antibody titer of the immunized animal to the inoculated antigen sufficiently increases (i.e., to have a titer of preferably 1,000,000 folds dilution or more by an ELISA method in the case of high-affinity antibody) and for at least a predetermined period (i.e., for at least 2 months in the case of high-affinity antibody). Thereafter, intravenous injection of only antigen to the immunized animal that showed a sufficient increase in titer of the antibody is carried out and after 3 days from the injection, spleen or lymph node that is considered to contain antibody-producing cells is collected, and spleen cells or lymphocytes are subjected to cell fusion with tumor cells. Thereafter, antibody-producing cells (hybridomas) immortalized by cell fusion are isolated. Generally, it is desirable that the tumor cells used here are obtained from the animal of the same species as that of the animal that has been subjected to immunization and from which the spleen, cells or lymphocytes have been prepared. However, tumor cells from animals of different species may also be used.

Examples of tumor cells that can be used include myeloma cells such as p3 (p3/x63-Ag8), P3U1, NS-1, MPC-11, SP2/0, FO, x63.6.5.3, S194, and R210. The cell fusion may be performed according to the generally employed method, for example, the method described in "Monoclonal Antibody Experimentation Manual" (Kodansha Scientific, 1987). The cell fusion may be performed by adding a cell fusion accelerator to a fusion medium in which the cells to be fused are suspended. The cell fusion accelerator includes sendai virus, polyethylene glycol having an average molecular weight of 1,000 to 6,000 and the like. In this case, an adjuvant such as dimethyl sulfoxide or cytokine such as IL-6 may be added to the fusion medium in order to further increase the efficiency of the fusion. For example, the mixing ratio of the tumor cells to the immunized spleen cells or lymphocytes may be such that the spleen cells or lymphocytes are about 1 fold to about 10 folds the tumor cells.

The fusion medium that can be used includes various commonly used media such as ERDF medium, RPMI-1640 medium, and MEM medium. At the time of fusion, it is generally recommended that fetal bovine serum (FBS) or other serum etc. be eliminated from the medium. Fusion is performed by well mixing predetermined amounts of the immunized spleen cells or lymphocytes and tumor cells with each other in the above-mentioned medium, adding from about 20% to about 50% of a polyethylene glycol solution, previously heated to about 37° C. and allowing the mixture to react preferably at from 30 to 37° C. for from about 1 to about 10 minutes. Subsequently, a suitable medium is added in succession, the mixture is centrifuged and the supernatant is removed. This procedure is repeated.

The target hybridoma is cultured in an ordinary selection medium, for example, HAI medium (a medium containing hypoxanthine, aminopterine, and thymidine). The culture in the HAI medium may be performed usually for from several days to several weeks, which is enough time for cells other than the target hybridoma (unfused cell etc.) to be killed. A technically important issue upon obtaining a soluble HAI-1-specific high-affinity monoclonal antibody is its screening. The screening of the hybridoma that produces soluble HAI-1-specific high-affinity monoclonal antibody can be achieved by analyzing the soluble HAI-1 or the like material obtained by the above-mentioned method by various immunochemical methods. For example, the binding of soluble HAI-1 used as an antigen for screening, to a monoclonal antibody secreted in the supernatant of hybridoma culture may be analyzed by an enzyme immunoassay such as an ELISA method or a Western blotting method to select the target hybridoma.

Specifically, the culture supernatant of the above-mentioned hybridoma is added to soluble HAI-1 adhered to, for example, a screening plate and blocked with BSA or the like to select a hybridoma that secretes an antibody capable of recognizing soluble HAI-1. For example, the culture supernatant of the selected hybridoma is added to a plate for the ELISA method to which soluble HAI-1 adheres and allowed to react and after sufficient washing operation, a labeled anti-murine IgG polyclonal antibody is added thereto, followed by further reaction. After one washing operation, the label is detected and the hybridoma whose culture supernatant is reactive with the soluble HAI-1-adhered plate is selected. The label that can be used includes various enzymes, fluorescent substances, chemiluminescent substances, radioisotopes, biotin, avidin and the like as will be described later.

The above-mentioned screening can give rise to a hybridoma that produces a monoclonal antibody that recognizes soluble HAI-1. On the other hand, upon screening such a hybridoma, reactivity with the above-mentioned partial sequence peptide may also be used as an index. The antibody produced by the hybridoma selected by such a method may be preferably further checked if it reacts with soluble HAI-1.

Although it has been reported that soluble HAI-1 includes molecular species having molecular weights of about 58,000, about 48,000, about 40,000 and about 39,000, respectively, the HAI-1-specific high-affinity monoclonal antibody of the present invention is not limited particularly as far as it has high affinity for soluble HAI-1 that has no cytoplasmic membrane-penetrating portion regardless of the molecular weight. However, it is preferred that the monoclonal antibody of the present invention binds to any of the above-mentioned soluble HAI-1's having respective molecular weights.

The soluble HAI-1-specific high-affinity monoclonal antibody of the present invention desirably has a dissociation constant with respect to soluble HAI-1 of $2 \times 10^{-9}$ M or less, preferably, $1 \times 10^{-9}$ M or less, and more preferably $5 \times 10^{-10}$ M or less.

The hybridoma clone that produces the above-mentioned soluble HAI-1-specific high-affinity monoclonal antibody specifically includes HAI-1A-1-1-3-4 described in Examples hereinbelow. In addition to HAI-1A-1-1-3-4, hybridomas that produce the soluble HAI-1-specific high-affinity monoclonal antibody of the present invention can be obtained with ease by referring to the description herein and using the methods well known to one skilled in the art.

By cloning the obtained hybridoma by a limiting dilution method, a single hybridoma clone that produces a monoclonal antibody can be obtained. This hybridoma clone is cultured in a medium containing from about 1% to about 5% of FBS from which bovine antibody (IgG) has been removed in advance or in a serum-free medium and the obtained culture supernatant is provided as a raw material for purifying the target monoclonal antibody. On the other hand, the obtained hybridoma clone may be transferred into the abdominal cavity of a Balb/C mouse or Balb/c(nu/nu) mouse previously administered with pristane and after from 10 to 14 days ascites containing the monoclonal antibody in a high concentration may be collected to provide a raw material for purifying the target monoclonal antibody. The monoclonal antibody may be purified by using an ordinary method for purifying immunoglobulins. For example, the purification may be performed by an ammonium sulfate fractionation method, a polyethylene fractionation method, an ethanol fractionation method, anion exchange chromatography, affinity chromatography bound to protein A or protein G, or the like.

<3> Preparation of Soluble HAI-1-Specific Polyclonal Antibody

The soluble HAI-1-specific high-affinity polyclonal antibody can be obtained by performing the procedure of subjecting the obtained polyclonal antibody derived from the immunized animal to operation for purifying an antibody that recognizes soluble HAI-1 by using HAI-1, preferably soluble HAI-1 or a partial peptide thereof as an antigen for immunization. As the antigen for immunization to obtain the polyclonal antibody, a fused form consisting of the above-mentioned HAI-1 partial sequence peptide and a carrier may also be used.

The animals to be used for immunization are not particularly limited and any one of rabbit, goat, sheep, mouse, rat, guinea pig, chicken, and the like may be used. Inoculation of the antigen for immunization to an animal is performed subcutaneously, intramuscularly, or intraperitoneally after well mixing the antigen for immunization with Complete Freund's adjuvant or Incomplete Freund's adjuvant. The inoculation is practiced every 2 weeks to 5 weeks and continued until the antibody titer of the immunized animal to the inoculated antigen sufficiently increases. Thereafter, intravenous injection of only antigen is performed to the immunized animal and after 3 to 5 days from the injection, antisera is obtained.

The polyclonal antibody may be purified from the obtained antisera by using an ordinary immunoglobulin purification method, for example, an ammonium sulfate fractionation method, a polyethylene fractionation method, an ethanol fractionation method, anion exchange chromatography, affinity chromatography bound to protein A or protein G, or the like.

The purification procedure for obtaining a soluble HAI-1-specific polyclonal antibody may be any method that can fractionate or purify a polyclonal antibody that recognizes soluble HAI-1 and examples of which include ion exchange chromatography, hydrophobic chromatography, molecular sieve chromatography, reverse phase chromatography, hydroxyapatite chromatography, affinity chromatography, gel electrophoresis, immunoelectrophoresis, etc. One specific example thereof is affinity column chromatography using a resin having immobilized thereon soluble HAI-1. For example, the polyclonal antibody obtained by the above-mentioned method used as a material may be subjected to affinity chromatography using the soluble HAI-1-immobilized resin. By this method, the polyclonal antibody that exists in the adsorption fraction bound to soluble HAI-1 is recovered.

By these methods, soluble HAI-1-specific polyclonal antibody can be obtained. In the method of affinity chromatography, a partial sequence peptide of soluble HAI-1 may be utilized. The peptide-immobilized resin may be used as a carrier for immobilization for affinity chromatography for use in purifying soluble HAI-1-specific polyclonal antibody.

Polyclonal antibodies have no dissociation constant in a strict sense. However, a value similar to the dissociation constant of soluble HAI-1 may be obtained by the procedure similar to that used for monoclonal antibody, that is, the method described in Example 4 hereinbelow. It is desirable that the soluble HAI-1-specific polyclonal antibody of the present invention has a value measured in such a manner of $2 \times 10^{-9}$ M or less, preferably, $1 \times 10^{-9}$ M or less, and more preferably $5 \times 10^{-10}$ M or less.

<4> Method of Specifically and Quantitatively Determining Soluble HAI-1

This method is a method of quantitatively determining soluble HAI-1 by using soluble HAI-1-specific high-affinity antibody of the present invention. The method of the present invention can be used in various diagnostic methods, measurement methods, assay methods for quantitatively determining HAI-1 in biological samples. The method is not particularly limited as far as quantitative determination of soluble HAI-1 is intended. The method includes, for example, a tissue staining method or an immune precipitation method for specifically detecting soluble HAI-1; a competitive binding assay for specifically measuring soluble HAI-1; or a direct or an indirect sandwich assay; two-antibody sandwich assay, and the like. The detection method includes enzyme immunoassay, radioimmunoassay, fluorescent immunoassay, chemiluminescent immunoassay, immunoblotting, immunochromatography, a latex agglutination method and the like.

Application examples of immunoblotting include use of microarray or chip having added or immobilized thereto a soluble HAI-1-specific high-affinity antibody. It is also possible to use soluble HAI-1-specific high-affinity antibody with a fluorescence label in a fluorescence deflection solution method or a fluorescence correlation variance method to detect the interaction with soluble HAI-1. Furthermore, it is possible to measure the interaction between the soluble HAI-1-specific high-affinity antibody and soluble HAI-1 by using a surface plasmon resonance apparatus. For example, soluble HAI-1 in a biological component can be quantitatively determined by allowing a biological sample containing soluble HAI-1 to flow through a surface plasmon resonance apparatus equipped with a sensor chip having bound thereto the soluble HAI-1-specific high-affinity antibody and tracking a change in time for a response signal.

The antibody used in the method of specifically measuring soluble HAI-1, for example, HAI-1-specific high-affinity antibody, may be used as it is, or it is possible to employ antibody in the form of Fab as obtained by papain treatment or in the form of $F(ab')_2$ or $F(ab')$ as obtained by pepsin treatment, both treatments being established methods. The fragments of the soluble HAI-1-specific high-affinity antibody are also embraced by the present invention. Such fragments include, for example, fragments containing a complementarity determining region (CDR) in both variable domains of H chain and L chain or hypervariable region of soluble HAI-1-specific high-affinity antibody.

The two-antibody sandwich assay that quantitatively determines soluble HAI-1 in a biological component includes a method of specifically measuring soluble HAI-1, comprising the steps of (1) reacting a reagent comprising one or a plurality of soluble HAI-1-specific high-affinity antibodies with soluble HAI-1 in a sample to generate an immune reaction product, (2) after separating the immune reaction product, reacting the immune reaction product with a labeled antibody that recognizes the soluble HAI-1 in the immune reaction product, and (3) measuring the labeled antibody bound to the immune reaction product; or a method of specifically measuring soluble HAI-1, comprising the steps of (1) reacting a reagent comprising soluble HAI-1 and a primary antibody consisting of one or a plurality of soluble HAI-1-specific high-affinity antibodies with soluble HAI-1 in a sample to generate an immune reaction product, (2) after separating the immune reaction product, reacting the immune reaction product with a secondary antibody that recognizes the soluble HAI-1 in the immune reaction product to generate an immune reaction product, (3) after separating the immune reaction product, reacting a labeled antibody that recognizes the secondary antibody in the immune reaction product, and (4) measuring the labeled antibody bound to the immune reaction product.

Specifically, soluble HAI-1-specific polyclonal antibody or soluble HAI-1-specific high-affinity monoclonal antibody as a primary antibody is immobilized to a solid phase such as micro-titer wells or micro-magnetic beads by a conventional procedure. Then, excessive protein binding site on the surface of the solid phase is blocked with bovine serum albumin, skimmed milk, gelatin or the like. Thereafter, the biological component containing soluble HAI-1 is added onto the surface of the solid phase to form an immune reaction product on the solid phase, followed by washing. Then, a labeled polyclonal antibody or a labeled monoclonal antibody that recognizes soluble HAI-1 as a secondary antibody was added and allowed to react. On this occasion, in the case where a monoclonal antibody was used as the primary antibody, a labeled soluble HAI-1-specific high-affinity monoclonal antibody having a different epitope than that of the primary antibody may be used as the secondary antibody. Further, after washing, the amount of the labeled antibody is measured to give a measured amount of the soluble HAI-1 in the biological component.

The label of the polyclonal antibody or monoclonal antibody as used herein may include enzymes such as alkaline phosphatase, horseradish peroxidase, β-galactosidase, urease, and glucose oxidase, and fluorescent substances such as fluorescein derivatives and rhodamine derivatives. In addition, the label may be rare earth elements or rare earth element complexes that enable time-resolved fluorometry, such as europium or europium complexes. Further, the label may be chemiluminescent substances such as acridinium esters or radioisotopes such as $^{125}I$, $^{3}H$, $^{14}C$, and $^{32}P$. That is, the present invention embraces quantitative determination of soluble HAI-1 in a biological component by using a method of determining color development, fluorescence, time-resolved fluorescence, chemiluminescence, electrochemical luminescence, or radioactivity. Also the present invention embraces labeling the secondary antibody with biotin and detecting alkaline phosphatase, horseradish peroxidase, β-galactosidase, urease, or glucose oxidase, fluorescein derivatives, rhodamine derivatives, rare earth element complexes, chemiluminescent substances such as acridinium ester, radioisotopes such as $^{125}I$, $^{3}H$, $^{14}C$, and $^{32}P$, forming a complex with avidin.

<5> Kit for Specifically and Quantitatively Determining or Staining Soluble HAI-1

A kit for specifically measuring soluble HAI-1 or a kit for specifically staining soluble HAI-1 is a kit for the diagnosis of diseases characterized by measuring or detecting soluble HAI-1. It has been revealed by the present invention for the first time that measuring soluble HAI-1 enables the diagnosis of patients in a state of diseases, for example, patients suffering from organopathy including glomerulonephritis, nephritis, hepatitis, pancreatitis, pneumonia, enteronitis, and gastritis, patients suffering from cancers, patients suffering from liver diseases, patients suffering from blood diseases, patients suffering from thrombosis including angina pectoris, myocardial infarction, and cerebral infraction. Therefore, measurement or detection of soluble HAI-1 enables to detect various diseases as described above. In the present invention, the kit for specifically measuring soluble HAI-1 is not particularly limited with regards to the material and method of constituting it as far as it is designed for specifically measuring the target soluble HAI-1.

Specifically, the kit of the present invention includes those kits that diagnose diseases by measuring or detecting soluble HAI-1 by using electrophoresis, HPLC method, various column chromatographic methods, various arrays, chips, or surface plasmon resonance apparatus, or the like. More specifically, the kit of the present invention includes a kit that measures or detects soluble HAI-1 by an immunological method using an antibody. The antibody that can be used includes at least one of the above-mentioned antibodies that recognize soluble HAI-1.

For example, in the case where the kit of the present invention is based on a two-antibody sandwich method, it includes a kit for specifically measuring soluble HAI-1 comprising the steps of (1) reacting a reagent comprising soluble HA1 and one or a plurality of soluble HAI-1-specific high-affinity antibodies with soluble HAI-1 in a sample to generate an immune reaction product, (2) after separating the immune reaction product, reacting the immune reaction product with a labeled antibody that recognizes the soluble HAI-1 in the immune reaction product, and (3) measuring the labeled antibody bound to the immune reaction product; or a kit of specifically measuring soluble HAI-1, comprising the steps of (1) reacting a reagent comprising soluble HAI-1 and a primary antibody consisting of one or a plurality of soluble HAI-1-specific high-affinity antibodies with soluble HAI-1 in a sample to generate an immune reaction product, (2) after separating the immune reaction product, reacting the immune reaction product with a secondary antibody that recognizes the soluble HAI-1 in the immune reaction product to generate an immune reaction product, (3) after separating the immune reaction product, reacting a labeled antibody that recognizes the secondary antibody in the immune reaction product, and (4) measuring the labeled antibody bound to the immune reaction product.

The kit comprises at least soluble HAI-1-specific high-affinity monoclonal antibody or soluble HAI-1-specific polyclonal antibody and may further comprise constituent elements necessary for the operation of detecting or measuring soluble HAI-1. Examples of the constituent elements include soluble HAI-1 as standard protein, enzyme, substrate and the like. The kit may contain the monoclonal antibody or polyclonal antibody in a state where it is bound to a label substance such as an enzyme or may contain a labeled antibody that recognizes the antibody. Furthermore, the kit may contain various kinds of suitable buffers, antigen dilutions, reaction dilutions, substrate solutions, reaction stop solution and the like. The kit of the present invention may include a vessel having a label and having encapsulated materials necessary for the detection and quantitative determination of soluble HAI-1. Examples of suitable vessel include vessels made of glass or various plastic materials such as polypropylene, polystyrene, polycarbonate, nylon, Teflon and the like. The kit preferably contains a manual that describes the method of detecting or measuring soluble HAI-1 in addition to the above-mentioned materials and vessel necessary for the detection or measurement of soluble HAI-1.

<6> Soluble HAI-1-Specific High-Affinity Antibody Associated with Human Diseases and Method of using the Same By using the method of using soluble HAI-1-specific high-affinity antibody and the kit therefor according to the present invention, soluble HAI-1 in the biological component collected from a patient in a state of a disease can be detected or quantitatively determined. The biological material from which soluble HAI-1 is detected is not particularly limited and any biological material such as tissue, blood serum, blood plasma, urine, serum, cerebrospinal fluid, tissue extract and the like may be applied after performing a suitable pretreatment. Detection or quantitative determination of soluble HAI-1 present in a biological material of a patient in a state of a disease enables diagnosis, prediction, or evaluate the progress of the disease. Examples of the disease include organopathy including glomerulonephritis, nephritis, hepatitis, pancreatitis, pneumonia, enteronitis, and gastritis, cancers, liver diseases, blood diseases, thrombosis including angina pectoris, myocardial infarction and cerebral infraction and the like.

In particular, examples of nephritis include mesangium proliferative nephritis, IgA nephritis, membraneous proliferative nephritis, membraneous nephritis, focal sclerosing glomerulopathy, acute renal failure, streptococcal acute glomerulonephritis, chronic/acute interstitial nephritis, nephrotic syndrome and the like. Examples of angina pectoris and myocardial infarction include stable angina of effort, unstable angina, acute myocardial infarction, inveterate myocardial infarction, and stable angina. It is possible to know the state of disease and prognosis of patients who received coronary artery intervention operation, transesophageal echocardiography, lower limb artery bypass operation, or aorta balloon pumping operation or patients suffering from acute aorta dissociation. Examples of cancers include hepatocellular carcinoma and pancreas cancer.

Since it is expected to exhibit the effect of specifically inhibiting the activity of soluble HAI-1, there is a reasonable expectation that the soluble HAI-1-specific high-affinity antibody can be used as a remedy for treating diseases caused by the soluble HAI-1.

For example, the soluble HAI-1 has the property of acting on inactive type HGFA to inhibit its activation. Therefore, the antibody that inhibits the inhibitory activity of soluble HAI-1 will increase the amount of active-type HGFA emerging in the living organism and further cause an increase in active type HGF. Since the active-type HGF is one of vascularization factors (Molecular Medicine of HGF, Medical Review Co. (1998)), such an antibody can be used as a remedy or preventive for angiopathy such as arteriosclerosis. The antibody used for this purpose is preferably humanized by using genetic engineering techniques. The humanization of antibody may be performed by the method well known to one skilled in the art as described in JP 11-506327 A.

By measuring the soluble HAI-1 in a biological component of patients, it is possible to make a judgment of effectiveness of medication and make a decision on the policy of therapy. It is often the case that a medicine effective to a disease is not always effective to all the patients or gives side effects since there are individual differences. Therefore, measurements of soluble HAI-1 before and after administration of a medicine enables practitioners to confirm the effectiveness and side effects of a medicine to individual patients to give them a guideline as to whether or not the therapy is continued by administering the medicine concerned.

EXAMPLES

Hereinafter, the present invention will be described in detail by way of examples. However, the present invention should not be construed as being limited thereto.

Example 1

Preparation of Soluble HAI-1-Specific High-Affinity Monoclonal Antibody

The soluble HAI-1 used as an immunogen, antigen for screening and a standard soluble HAI-1 in the soluble HAI-1 measurement system was obtained by having expressed and secreted by recombinant CHO cells created by utilizing HAI-1 cDNA, and purifying it by column chromatography.

A solution containing 100 µg of soluble HAI-1 together with the same volume of Freund's complete adjuvant or Freund's incomplete adjuvant was administered to the endothelium and hypodermis of Balb/c mice 3 times at intervals of 4 weeks. After confirming production of soluble HAI-1-specific high-affinity antibody in the blood serum of the mouse, a solution containing 30 µg of soluble HAI-1 was administered through caudal vein. After 3 days, the spleen was extracted and spleen cells were subjected to cell fusion with myeloma cells P3U1 by using polyethylene glycol 1500 according to the method described in "Monoclonal Antibody Experimentation Manual" (Kodansha Scientific (1987)) and the fused cells were dispensed into the wells of a 96-well plate, followed by adding HAI medium and incubating the cells for 14 days.

Thereafter, screening of hybridomas that produce monoclonal antibodies specific to the soluble HAI-1 in the medium was performed. That is, to an ELISA plate for screening soluble HAI-1-specific high-affinity antibody having immobilized thereon the soluble HAI-1 and blocked with BSA was added the culture supernatant of hybridomas to be selected and the reactivity of monoclonal antibodies present in the culture supernatant was analyzed. After the culture supernatant of hybridomas to be selected was added to the ELISA plate for screening in an amount of 100 µl/well, the reaction is continued for 1 hour or more.

Thereafter, the wells of the plate were thoroughly washed with PBS(−) solution containing 0.05% Tween 20 (hereinafter abbreviated as "PBST solution"), and then 100 µl/well of PBS(−) containing 1 µg/ml of HRP (horse radish peroxidase)—labeled goat anti-murine IgG Fc polyclonal antibody (available from ICN Co.) and 1% BSA was added to the wells and allowed to react at room temperature for 1 hour. After thoroughly washing with PBST solution, citrate-phosphate buffer (pH 5.0) containing 0.4 mg/ml o-phenylenediamine (OPD, P-9029, trade name, manufactured by Sigma AB) and 0.015 to 0.03% hydrogen peroxide solution was added and allowed to react at room temperature to effect color development. Thereafter, 1N $H_2SO_4$ solution was added to stop the reaction and measurement of the reaction mixture was performed at a measurement wavelength of 490 nm and a reference wavelength of 650 nm.

Then, each of the obtained hybridoma reactive with the soluble HAI-1 was cloned 3 times by limiting dilution and thereafter the culture supernatant was recovered and subjected to purification of monoclonal antibodies by affinity chromatography using immobilized protein A column (manufactured by Amersham Pharmacia Biotech AB).

A strain of the hybridoma clone thus cloned was named HAI-1A-1-1-3-4. HAI-1A-1-1-3-4 was deposited at International Patent Organism Depositary (IPOD), National Institute of Advanced Industrial Science and Technology (Chuo 6, 1-1, Higashi 1-chome, Tsukuba-shi, Ibaraki-ken, Postal Code: 305-8566, Japan) on Oct. 19, 2001 under the accession number FERM P-18565 and transferred from the original deposit to an international deposit on Apr. 17, 2002 under Budapest Treaty and assigned the accession number FERM BP-8022.

Example 2

Preparation of Polyclonal Antibody to Soluble HAI-1 and of its Labeled Form

Polyclonal antibody to soluble HAI-1 was prepared as follows. That is, a mixture consisting of a solution containing 100 µg of soluble HAI-1 and the same volume of Freund's complete adjuvant or Freund's incomplete adjuvant as antigen was subcutaneously administered to a rabbit 7 times at intervals of 2 weeks. After confirming production of an antibody in the blood serum, additional 10 µg of the antigen was intravenously administered and after 5 days, antiserum was obtained. Further, after precipitation treatment with ammonium sulfate, the antiserum was purified by using a protein A column to obtain anti-soluble HAI-1 polyclonal antibody. Thereafter, the obtained anti-soluble HAI-1 polyclonal antibody was labeled with biotin to obtain biotin-labeled anti-soluble HAI-1 polyclonal antibody.

Example 3

Construction of Soluble HAI-1 Quantitative Determination System

The monoclonal antibody produced by the hybridoma clone HAI-1A-1-1-3-4 prepared in Example 1 and conventional monoclonal antibodies C76-18 and 1N7 were used as primary antibodies. Each monoclonal antibody was dissolved in 0.05 M carbonate-hydrogen carbonate buffer (pH 9.6) to a concentration of 20 µg/ml and added to the wells of a 96-well plate in an amount of 50 µl/well and the plate was left to stand at 4° C. overnight (about 12 hours or more) or at 37° C. for 2 hours or more. After removing the primary antibody solution from the primary antibody-attached plate, 250 to 300 µl/well of 1% BSA-containing PBS(−) was added to the wells and the plate was left to stand at 4° C. overnight (about 12 hours or more) or at 37° C. for 2 hours or more to effect blocking operation. After removing the blocking solution from the plate, 50 µl/well of soluble HAI-1 of varying concentration (0, 0.625, 1.25, 2.50, 5.00, 10.0, 20.0, or 40.0 ng/ml) dissolved in 20 mM sodium phosphate buffer (pH 7.5) containing 0.15 M NaCl, 0.05% Tween 20, and 1% BSA was added to the wells per time and allowed to react at room temperature for 1 hour.

Thereafter, the wells were thoroughly washed with a washing solution having a composition consisting of 500 mM NaCl, 0.05% Tween 20 and 20 mM Tris-HCl (pH 7.5)

and then 100 µl/well of PBS(−)containing 10 µg/ml of the biotin-labeled anti-soluble HAI-1 polyclonal antibody prepared in Example 3 and 1% BSA was added to the wells and allowed to react at room temperature for 1 hour.

After thoroughly washing the wells with the above-mentioned washing solution, 100 µl/well of PBS(−) containing 1% BSA with 2,000-fold dilution of HRP-labeled streptoavidin (manufactured by Amersham Pharmacia Biotech AB, Code RPN1231) was added to the wells and allowed to react at room temperature for 1 hour. After thoroughly washing the wells with the above-mentioned washing solution, 100 µl/well of citrate-phosphate buffer (pH 5.0) containing 0.4 mg/ml of o-phenylenediamine (OPD, P-9029, manufactured by Sigma AB) and 0.015 to 0.03% hydrogen peroxide solution was added to the wells and allowed to react at room temperature to effect color development.

Thereafter, 100 µl/well of 1N $H_2SO_4$ solution was added to the wells to stop the reaction and the measurement was performed at a measurement wavelength of 490 nm and a reference wavelength of 650 nm. The results are shown in FIGS. 1A and 1B. FIG. 1A illustrates the reactivity of each monoclonal antibody with soluble HAI-1 in a concentration of soluble HAI-1 in a range of from 0 to 40 ng/ml. FIG. 1B is an illustration in an enlarged view of the reactivity in a range of from 0 to 2.5 ng/ml out of the range shown in FIG. 1A. For only the hybridoma clone HAI-1A-1-1-3-4, a concentration-dependent reaction curve could be obtained but the conventional antibodies C76-18 and 1N6 showed no reactivity.

Example 4

Measurement of Dissociation Constant of HAI-1-Specific High-Affinity Monoclonal Antibodies The monoclonal antibody derived from hybridoma clone HAI-1A-1-1-3-4 out of the soluble HAI-1-specific high-affinity monoclonal antibodies prepared and purified in Example 1, and the conventional antibodies C76-18 and 1N7 were measured for dissociation constant. To a soluble HAI-1-immobilized plate obtained by immobilizing soluble HAI-1 to a plate and blocking it with BSA was added each antibody in a differing concentration, which was allowed to react until an equilibrium was reached (for 2 hours or more).

Thereafter, the wells of the plate was thoroughly washed with PBS(−) solution containing 0.05% Tween 20 (hereinafter abbreviated as "PBST solution"), 100 µl/well of PBS (−) containing 1 µg/ml of HRP (horse radish peroxidase)—labeled goat anti-murine IgG *Fc polyclonal antibody (available from ICN Co.) and 1% BSA was added to the wells and allowed to react at room temperature for 1 hour. After thoroughly washing with PEST solution, citrate-phosphate buffer (pH 5.0) containing 0.4 mg/ml o-phenylenediamine (OPD, P-9029, manufactured by Sigma AB) and 0.015 to 0.03% hydrogen peroxide solution was added and allowed to react at room temperature to effect color development.

Thereafter, 1 N $H_2SO_4$ solution was added to stop the reaction and measurement of the reaction mixture was performed at a measurement wavelength of 490 nm and a reference wavelength of 650 nm. From the measurement results, scattered plotting was performed to obtain dissociation constants. The results are shown in Table 1. The monoclonal antibody obtained by the present invention showed the smallest dissociation constant, that is, the highest affinity.

TABLE 1

| Antibody | Dissociation constant |
|---|---|
| HAI-1A-1-1-3-4 | $2.67 \times 10^{-10}$ |
| C76-18 | $1.48 \times 10^{-9}$ |
| 1N7 | $1.68 \times 10^{-8}$ |

The values were expressed in molarity [mol/l]

Example 5

Measurement of HAI-1 in Blood of Healthy Person

By using the HAI-1-specific highly sensitive measurement system prepared in Example 3, soluble HAI-1 in blood sera from 56 healthy persons were measured. The blood sera from healthy persons were stored under freezing after the extraction and used by thawing just before the experiments. First, 50 µl/well of 20 mM sodium phosphate buffer (pH 7.5) containing 015 M NaCl, 0.05% Tween 20, and 1% BSA was added to the wells of the 96-well plate to which the primary antibody adhered and which was blocked prepared in Example 3 and then 50 µl/well of blood serum from a healthy person or standard soluble HAI-1 of varying concentration (0, 0.625, 2.50, 5.00, 10.0, or 40.0 ng/ml) was added to the wells, followed by allowing to react at room temperature for 1 hour. Then the wells were washed with a washing solution having a composition of 500 mM NaCl, 0.05% Tween 20 and 20 mM Tris-HCl (pH 7.5). Thereafter, 100 µ/well of PBS(−)containing 10 µg/ml of the biotin-labeled anti-soluble HAI-1 polyclonal antibody prepared in Example 3 and 1% BSA was added to the wells and allowed to react at room temperature for 1 hour. After thoroughly washing the wells with the above-mentioned washing solution, 100 µl/well of PBS(−) containing 1% BSA with 2,000-fold dilution of HRP-labeled streptoavidin (manufactured by Amersham Pharmacia Biotech AB, Code RPN 1231) was added to the wells and allowed to react at room temperature for 1 hour.

Figure 2:
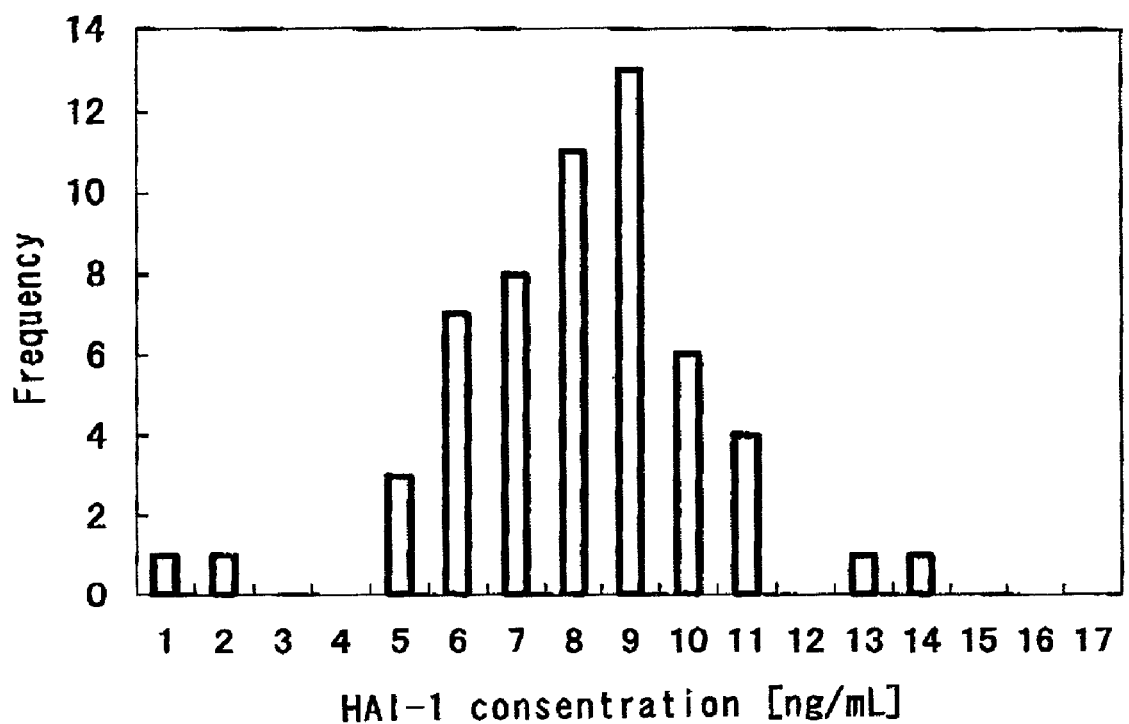
FIG. 2 is a diagram showing the amount of HAI-1 in blood serum of a healthy person in a histogram.

After thoroughly washing the wells with the above-mentioned washing solution, citrate-phosphate buffer (pH 5.0) containing 0.4 mg/ml of o-phenylenediamine (OPD, P-9029, manufactured by Sigma AB) and 0.015 to 0.03% hydrogen peroxide solution was added to the wells and allowed to react at room temperature to effect color development. Thereafter, 100 µl/well of 1N $H_2SO_4$ solution was added to the wells to stop the reaction and the measurement was performed at a measurement wavelength of 490 nm and a reference wavelength of 650 nm. Then a calibration curve was prepared from the concentration of standard soluble HAI-1 and an amount of developed color, and the concentration of soluble HAI-1 in the blood sera of healthy persons was calculated. FIG. 2 shows the results obtained. In the blood sera of healthy persons (number of samples: 56), the concentration of soluble HAI-1 was in a range of from 0 to 13.5 ng/ml, with the average being 7.5 ng/ml.

Example 6

Measurement of HAI-1 in Patients Suffering from Various Diseases

By using the HAI-1-specific highly sensitive measurement system prepared in Example 3, soluble HAI-1 in the blood sera from patients suffering from various diseases was measured by the method described in Example 5. The number of patients was 5 for each disease. Each blood serum was stored under freezing after extraction and used by thawing just before the experiments. Table 2 shows the results obtained. It revealed that in the bloods of patients suffering from nephritis, hepatitis, pancreatitis, lung cancer, liver cancer, myocardial infarction, cerebral infarction, hepatocellular carcinoma and pancreas cancer, soluble HAI-1 existed in concentrations higher than those in the bloods of healthy persons (number of samples: 56, average value: 7.5 ng/ml).

TABLE 2

| Case | Patient 1 | Patient 2 | Patient 3 | Patient 4 | Patient 5 |
|---|---|---|---|---|---|
| Nephritis | 67.0 | 43.3 | 31.7 | 28.1 | 25.7 |
| Hepatitis | 85.6 | 75.8 | 67.7 | 61.8 | 60.6 |
| Pancreatitis | 40.8 | 29.4 | 24.9 | 23.8 | 23.4 |
| Lung cancer | 60.2 | 49.7 | 45.7 | 38.0 | 37.4 |
| Liver cancer | 53.7 | 50.9 | 47.4 | 32.8 | 28.3 |
| Myocardial infarction | 20.7 | 19.9 | 17.8 | 15.8 | 15.4 |
| Cerebral infarction | 48.5 | 38.8 | 35.1 | 30.0 | 17.5 |
| Hepatocellular Carcinoma | 29.5 | 30.9 | 73.6 | 42.0 | 33.3 |
| Pancreas cancer | 22.0 | 61.3 | 24.4 | 27.7 | 74.1 |

The values indicate concentrations of soluble HAI-1 [ng/ml].

The application is based on Japanese patent application No. 2001-157082 which was filed on May 25, 2001 and Japanese patent application No. 2002-7443 which was filed on Jan. 16, 2002.

What is claimed is:

1. An antibody that has an ability to recognize and quantitatively bind to soluble hepatocyte growth factor activator inhibitor-1 (soluble HAI-1) in a body fluid when used in a two-antibody sandwich assay, wherein the antibody has a dissociation constant to soluble HAI-1 of $5 \times 10^{-10}$ M or less and is a monoclonal antibody produced by a hybridoma of accession number FERM BP-8022, and wherein the soluble HAI-1 has a molecular weight of about 39,000 to 58,000 daltons as measured by SDS-PAGE under reduced conditions.

2. A hybridoma cell line that produces a monoclonal antibody according to claim 1 and is a hybridoma of accession number FERM BP-8022.

3. A method of quantitatively determining soluble HAI-1 in a body fluid, comprising immunologically measuring the soluble HAI-1 by using at least one antibody according to claim 1.

4. The method according to claim 3, wherein a sample in which soluble HAI-1 is to be measured is a body fluid collected from a subject or animal.

5. The method according to claim 4, wherein the body fluid is blood or its fractionation product or a treated product.

6. The method according to claim 4, wherein the body fluid is plasma or blood serum.

7. The method according to claim 4, wherein the body fluid is urine.

8. A kit for detecting or quantitatively determining soluble HAI-1, comprising at least one antibody according to claim 1.

9. The kit according to claim 8, wherein the detection or quantitatively determination of the soluble HAI-1 is performed by immunological staining.

* * * * *